United States Patent
Dwork et al.

(10) Patent No.: US 6,248,096 B1
(45) Date of Patent: Jun. 19, 2001

(54) MALE URINARY INCONTINENCE DEVICE HAVING EXPANDABLE FLUTES

(75) Inventors: Paul Dwork, 1127 Garrido Dr., Camarillo, CA (US) 93010; Edward E. Elson, Anaheim, CA (US)

(73) Assignee: Paul Dwork, Camarillo, CA (US)

( * ) Notice: Subject to any disclaimer, the term of this patent is extended or adjusted under 35 U.S.C. 154(b) by 0 days.

(21) Appl. No.: 09/459,402

(22) Filed: Dec. 8, 1999

Related U.S. Application Data

(63) Continuation-in-part of application No. 09/262,523, filed on Mar. 4, 1999, now Pat. No. 6,113,582.

(51) Int. Cl.$^7$ .................................................. A61F 5/44
(52) U.S. Cl. ........................ 604/349; 604/347; 604/351
(58) Field of Search .................................. 604/345–347, 604/349–353, 355; 128/760, 842, 844, 918; 600/38–39, 41

(56) References Cited

U.S. PATENT DOCUMENTS

| | | |
|---|---|---|
| 719,811 | 2/1903 | Kent . |
| 1,105,488 | 7/1914 | Clare . |
| 2,310,505 | 2/1943 | Blackburn et al. . |
| 2,445,694 | 7/1948 | Predmore . |
| 3,526,227 | 9/1970 | Appelbaum . |
| 4,553,968 | 11/1985 | Komis . |
| 4,601,716 | 7/1986 | Smith . |
| 4,713,067 | 12/1987 | Rothenberg et al. . |
| 4,790,834 | 12/1988 | Austin . |
| 4,961,734 * | 10/1990 | Kassman ............................... 604/349 |
| 4,997,427 | 3/1991 | Bowen . |
| 5,009,649 | 4/1991 | Goulter et al. . |
| 5,032,118 | 7/1991 | Mason . |
| 5,065,459 | 11/1991 | Tjahaja et al. . |
| 5,094,230 * | 3/1992 | Cllark, Jr. ............................... 600/38 |
| 5,147,341 | 9/1992 | Starke et al. . |
| 5,195,997 | 3/1993 | Carns . |
| 5,205,298 * | 4/1993 | Hurst . |
| 5,267,989 | 12/1993 | Moyet-Ortiz . |
| 5,346,483 | 9/1994 | Thaxton, Sr. . |
| 5,366,449 | 11/1994 | Gilberg . |
| 5,423,785 * | 6/1995 | Hart ....................................... 604/353 |
| 5,437,652 * | 8/1995 | Anatolievich . |
| 5,478,334 * | 12/1995 | Bernstein . |
| 5,618,277 * | 4/1997 | Goulter ................................. 604/349 |
| 5,643,235 | 7/1997 | Figuerido . |
| 5,662,631 * | 9/1997 | Matx . |
| 5,695,485 | 12/1997 | Duperret et al. . |
| 5,797,890 * | 8/1998 | Goulter ................................. 604/351 |

* cited by examiner

Primary Examiner—Richard K. Seidel
Assistant Examiner—LoAn H. Thanh
(74) Attorney, Agent, or Firm—Shanks & Herbert

(57) ABSTRACT

An apparatus for forming a fluid tight seal around a penis of a user comprising for controlling male urinary incontinence, the apparatus having a substantially fluid impermeable sheath having a proximal end and a distal end, an inner surface and an outer surface, wherein, in use, at least a portion of the inner surface contacts the skin of the penis. The sheath has a first longitudinally compliant portion and a second radially compliant portion positioned between the proximal and distal ends. The longitudinally compliant portion can take the form of bellows, and the radially compliant portion can take the form of flutes. A retention arrangement, such as a strap for retaining the radially compliant portion about the circumference of the penis of a user can also be provided. The sheath is, in use, attached at the proximal end to a retention ring attached to a user.

18 Claims, 14 Drawing Sheets

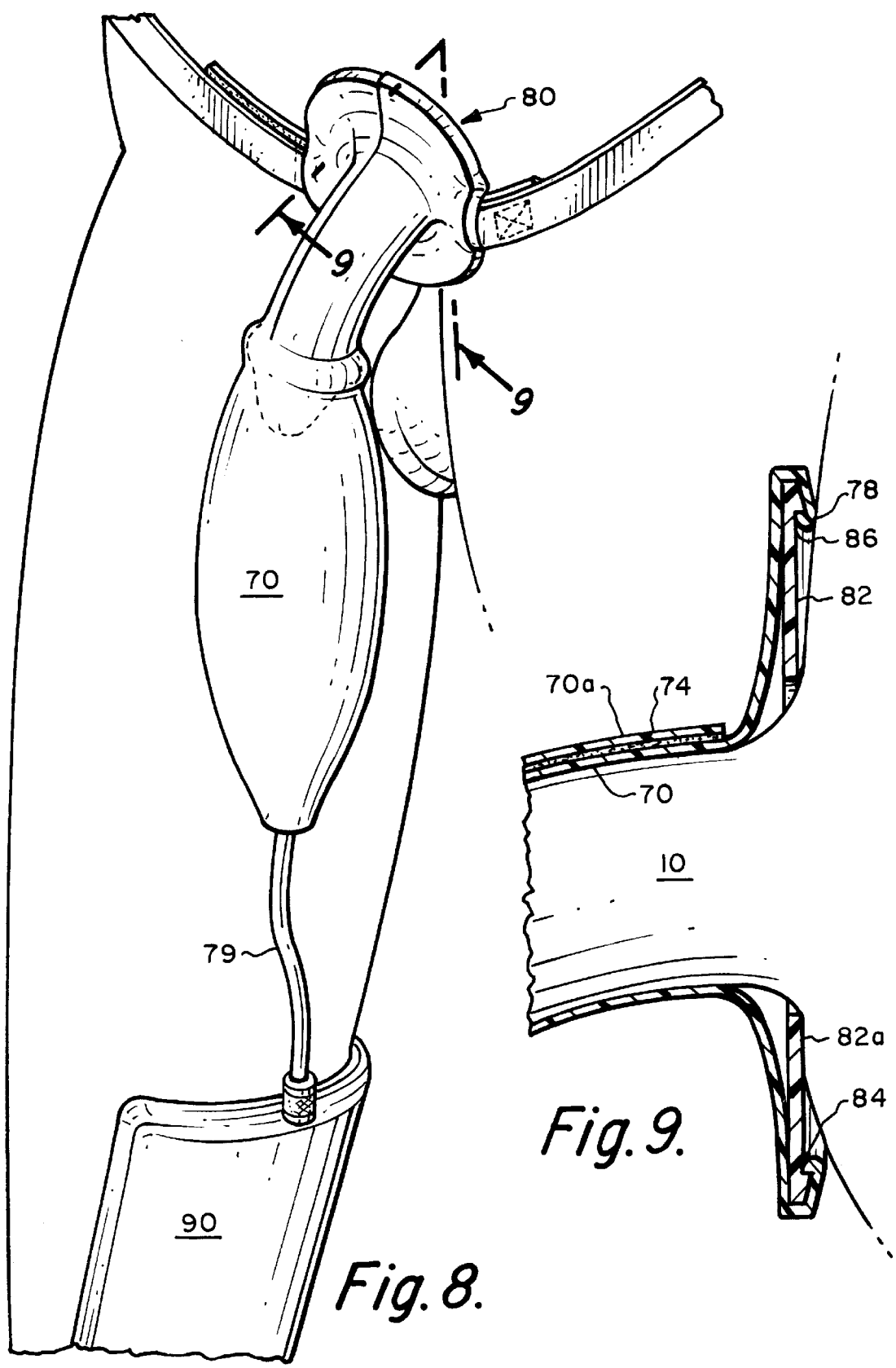

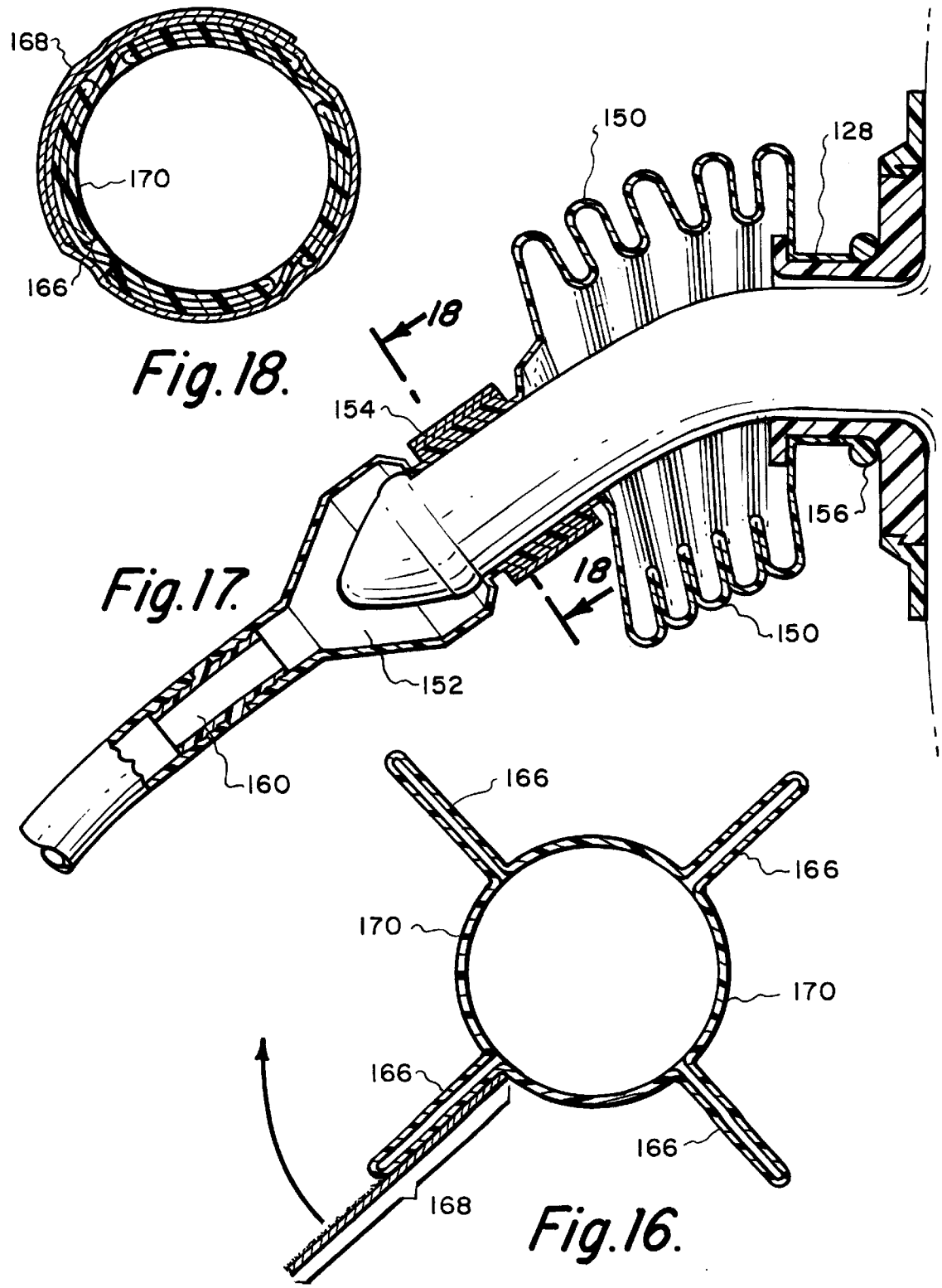

MALE URINARY INCONTINENCE DEVICE HAVING EXPANDABLE FLUTES

This application is a continuation-in-part of U.S. Ser. No. 09/262,523 filed Mar. 4, 1999 which is now U.S. Pat. Ser. No. 6,113,582, the contents of which are incorporated herein by reference.

BACKGROUND OF THE INVENTION

1. Field of the Invention

The present invention relates to urinary incontinence in general, and more specifically to a male urinary incontinence device using a wrap for enveloping the penis.

2. Background

Urinary Incontinence (UI) is a very common problem in the United States estimated to afflict more than 13 million people. Of those afflicted, about one third are men. The total annual cost of providing care for persons with UI is estimated to be $16 billion. The market for adult absorbent devices or diapers alone in 1994 was $1.5 billion projected to be growing about 25% per year. As the demographics in the United States shift to a more aged population, and as society in general becomes increasingly mobile, the increasing number of persons suffering from, and demanding solutions for UI will simultaneously increase.

UI can affect persons of all ages, and may be the result of physical disability or a psychological condition. There are several different types of incontinence, which are outlined below.

Acute (or Transient) Incontinence is caused by generally treatable medical problems. Medical conditions such as dehydration, delirium, urinary retention, fecal impaction/constipation, urinary tract infection and atrophic vaginitis can cause an onset of UI. In addition to medical problems, certain medications can cause or contribute to an incontinence problem, such as anticholinergic agents, antihistamines, antidepressants (TCA), phenothiazines, disopyramides, opiates, antispasmodics, Parkinson drugs, alpha-adrenergic agents (high blood pressure drugs), sympathomimetics (decongestants), and sympatholytics (e.g., prazosin, terazosin, and doxazosin).

Chronic UI is by definition an ongoing and therefore more difficult to treat affliction. Chronic UI is conventionally classified into four groups: Stress, Urge, Overflow, and Functional incontinence. They may occur alone or in combination, the latter being more common as the patient ages.

Stress incontinence is the involuntary leakage of small amounts of urine in response to increased pressure in the abdomen. Incontinence will usually occur during physical events, such as sneezing, coughing, laughing, bending, lifting, etc. Although stress incontinence is predominantly a female affliction, men can also suffer from stress incontinence. Stress incontinence in men usually results from a weakened function of the urethral sphincter that surrounds the prostate, sometimes as a result of prostate surgery.

Urge incontinence is the most common pattern of UI in middle aged and older people, and is characterized by insufficient control during the time between the urge to void and the start of urination. One cause of urge UI is detrusor hyperreflexia or instability which is associated with disorders of the lower urinary tract or neurologic system. Urge incontinence can also be the result of urologic carcinoma, diverticula, or other physical abnormalities.

Overflow incontinence accounts for 10–15% of urinary incontinence. Overflow UI is usually the result of an obstruction. (e.g., enlarged prostate, urethral stricture) of the bladder outlet or an atonic bladder as the result of neurologic injury (e.g., spinal chord trauma, stroke), diabetic neuropathic bladder, or drug-induced atonia. The obstruction leads to bladder overfilling, resulting in a compulsive detrusor contraction. In this form of UI chronic "dribbling" is common. Drug induced atonia can be caused by anticholinergics, narcotics, anti-depressants, and smooth muscle relaxants.

Functional incontinence accounts for 25% of all incontinence and results when a person is confined and sedentary, such as in a nursing home or during a long period of convalescence. Functional incontinence is sometimes diagnosed as a result of the individual simply being unable to communicate his or her needs, or through other sensory impairments that make the individual unaware of his or her need to void. This condition can further result from decreased mental function, decreased functional status, and/or a simple unwillingness to physically go to the toilet.

Incontinence is also frequent among persons rehabilitating from stroke, head injury, multiple sclerosis, amputations, and spinal cord injury.

Enuresis, or bedwetting, is a form of incontinence that is very common among preschool children, and often persists into adulthood. Enuresis can cause degraded self-esteem, and may lead to social withdrawal at an early age. The bedwetter may be reluctant to attend sleep over social events with his or her friends. Most often, the reason a child or adult will have the problem of nocturnal enuresis is because they simply cannot wake up. Nocturnal enuresis afflicts approximately 15–20% of school age children between the ages of 4 and 16. Treatment of enuresis typically requires training the person to recognize the need to urinate during sleep, or to train the person to sleep correctly. Moisture sensing alarms have been successfully employed, but if soiled bedding are to be avoided, require the use of diapers or other absorbent padding.

Some symptoms of UI that interfere with quality of life include leaking urine when coughing, sneezing, laughing or exercising; waking up multiple times at night to go to the bathroom; the need to know the locations of bathrooms when on travel or shopping; and the leaking of urine during sex. UI can obviously lead to discomfort and embarrassment, and eventually to social withdrawal and isolation. Excursions outside the home, social interaction, and sexual activity may be restricted or avoided entirely in the presence of incontinence. In older persons, UI is the predominant reason aging parents are put into nursing homes, because of the burden UI places on caregivers.

Means for aiding incontinence in the prior art include catheterization, absorbent products, and for males, devices attached to the exterior surface of the penis to collect urine discharge. For children prone to bedwetting, various approaches are also available, for example wet-bed alarm systems, which are readily available and easy to use, and Desmopressin acetate (synthetic ADH), a nasal spray.

Catheterization is an unattractive option to many persons suffering from UI because of the risks associated with an indwelling catheter. The catheter may be retained permanently in the bladder draining freely into a collection bag. In the permanent arrangement, the catheter is held in the bladder by a balloon, usually inflated with sterile water. The catheter may also be inserted intermittently on an as-needed basis. This approach is very inconvenient and many patients are psychologically averse to self-catheterization, or physically unable to perform the manipulations required.

Long term use of indwelling catheters presents further problems. Within 2 to 4 weeks after permanent catheterization, the urine of virtually every patient is contaminated by bacteria. Catheter-associated bacteriuria represents the most common infection acquired in acute care and long-term care facilities. Complications ranging from bladder spasms and catheter leakage to death caused by septicemia are also well known limitations. Bacterial entry into the bladder occurs either from extraluminal migration along the outside of the catheter, contamination on insertion of the catheter, or contamination of the drainage bag, leading to bacterial growth and subsequent migration into the bladder.

Accordingly, catheterization is overall the least preferred type of bladder management.

Absorbent devices, such as diapers, are the most popular remedy, accounting for billions of dollars in annual sales in the US. They are easily obtained, and can address acute UI symptoms quickly. While affording somewhat effective control of urine and providing mobility to the patient, the absorbent method suffers from very serious drawbacks.

First, absorbent devices do not remove urine to a point distal from the genital region, they simply absorb and disperse the urine in order to manage it. This, of course, leads to urine soaked absorbent being in contact with the skin, which causes irritation and discomfort. Most advances in the art deal with providing different absorbent layers to attempt to direct the urine to migrate to a region away from the skin, with limited success.

Absorbent devices also disadvantageously rely on providing a large area of absorbent, usually in the form of pants or diapers. Not only is such an arrangement uncomfortable, it requires involved procedures for applying and removing the device. Further, the diaper pants must be removed in order to defecate, apply medications to the groin area, etc. Once removed, whether soiled or not, the disposable-type diaper usually must be disposed of, creating the need to always carry a supply of such absorbent devices.

A major problem with absorbent devices is that of odor. Urine has a distinctive and recognizable odor which is embarrassing to most people. Various approaches have been taken in order to control urine odor with absorbent devices, with limited success.

In men, an alternative to the indwelling catheter or absorbent device is an external collecting device which is fitted over the male genitalia, like a condom, and connected via a tube to a drainage bag held onto the body by leg straps, or by special devices like the one leg pant marketed by NETTI®, as well as bedside drainage bags which are available while one in bed. Several such "external catheter" devices are described in the prior art.

U.S. Pat. Nos. 5,797,890 and 5,009,649 describe male UI condom catheters. In these type devices, a latex or similar material condom is unrolled onto the penis, sealingly engaging the same. An extended fluid collection region extending from the distal end of the device provides a reservoir for collected urine. The condom is additionally held to the penis by means of a band, for example using VELCRO®. The '890 patent additionally provides a ring mounted on a simple garment support that allows the rolled, proximal end of the condom to be unrolled about the ring, allowing additional support of the device, but requiring that the frequently flaccid penis be inserted under axial load into the condom.

These devices are disadvantaged by the complexity of their application, and the requirement that the condoms be properly sized for the device to function properly. The application of the condom member requires some degree of dexterity to position and unroll the condom onto the penis, which is frequently flaccid. The flaccid state of the penis renders the seal created by the condom variably effective, and frequently inadequate. Further, in the case of a patient deprived of the full use of his motor skills, for example a stroke patient or MS sufferer, the task may be impossible. Frequently, the issue of condom sizing creates difficulties, when the purchaser is other than the user, or when the user is less than sure about his relative girth.

A further severe disadvantage with this type of device is that should the evacuation tube at the distal end of the condom become kinked or blocked, urine pressure will build in the condom until urine is forcefully ejected along the side of the condom, the condom breaks, or the entire apparatus slips from the penis. The spread of urine up the shaft of the penis lowers the friction between the condom and the penile shaft, increasing the chances of the penis slipping from the condom. Such events can be extremely messy, causing the forceful discharge of a substantial amount of urine into the pants of the wearer.

Other devices comprise a loose-fitting sleeve for the penis, such as the McGuire style mail urinal. The urinal, which is in effect a bag into which the penis extends, is used in conjunction with a valved tube leading to a leg bag. In theory, the urinal drains into the leg bag. These devices create serious problems with poor sealing and spillage of urine around the penis, and even present the problem of a flaccid and withdrawn penis pulling out of the sleeve altogether. Because the device relies on gravity to feed urine from the urinal to the leg bag, use during sitting can be messy or uncomfortable.

Improvements to the prior art are continually being sought.

SUMMARY OF THE INVENTION

The present invention provides a male urinary incontinence device which overcomes the problems of the prior art. The invention permits facile, one-handed mounting onto any sized male member, even if flaccid and withdrawn, and provides for positive sealing and isolation of the skin and the outside environment from urine. The invention also permits compensation for changes in penile length and diameter over time by providing flexibly compliant portions longitudinally spaced along the penile shaft.

According to the invention, a fluid tight wrap is provided around a penis of a user utilizing a substantially fluid impermeable sheath formed of sheet material. The sheath has a proximal end and a distal end, an inner surface and an outer surface, where the inner surface contacts the skin of the penis in use. The sheath has a first side and a second side, and sheath member is sized to circumferentially envelop a penis of a user such that the inner surface of the second side overlaps the attachment portion and the attachment portion securing the second side to the first side such that the first and second sides overlyingly coextend substantially longitudinally down the penile shaft from the proximal end of the sheath to the distal end of the sheath.

In an alternative embodiment of the invention, the sheath can also have one or more, for example two, compliant portions which extend longitudinally down and circumferentially around the penile shaft from the proximal end of the sheath to the distal end of the sheath. The first expandable portion can be, for example, in the form of bellows which can expand in response to penile enlargement, in an accordion-like manner. The second expandable portion is adjacent to the distal end of the sheath, and can be, for example, in the form of expandable flutes that are adjustable according to penile size, in particular accommodating differences in penile diameter.

Features of the invention include a relatively flat bearing ring for surrounding the penis at the base of the shaft for advantageously posturing the penis for application of a penis sheath. The ring advantageously provides a stable surface that covers the pubic hair area by being held against the body surface once the penis has been inserted, which allows for correct mounting of the remaining parts of the apparatus. The ring can be rigid, semi-rigid, or other configurations between rigid an soft, and can be flat or convex or concave. The ring can optionally be supplied as a separate entity from the sheath, so that the ring can be conveniently selected depending on the size of the penis.

A further feature of the invention includes a sheath which is wrapped about the penis, distributing sealing pressure evenly over the surface of the organ.

A still further feature of the invention is a separate urine chamber, which sealingly attaches to the exterior of the sheath and to a bag or the like.

A feature of the alternative embodiment of the invention is a penile chamber, which advantageously conforms to the shape of the head of the penis so that urine will be encouraged to flow out naturally and not back up the penis. The penile chamber permits attachment of urine collection bags or chambers if desired, and any other attachment to ease collection and/or flow of urine away from the patient body.

A further feature of the invention includes a closed system for handling urine from a patient suffering from urinary incontinence, thus eliminating unpleasant odor.

An advantage of the present invention is a one size fits all approach that allows for simpler and less embarrassing purchasing decisions.

A further feature of the present invention is a male UI device which can be made as a daily disposable device or one which is reusable and economical to maintain.

Yet another advantage of the instant invention is that it is usable with bedwetting alarms, allowing corrective training of children without soiled bedding.

BRIEF DESCRIPTION OF THE DRAWINGS

The foregoing and other features and advantages of the present invention will be more fully understood from the following detailed description of an illustrative embodiment, taken in conjunction with the accompanying drawing in which:

FIG. 8 is a perspective view of the integrated sheath and primary fluid chamber of FIG. 8 mounted on a patient and connected to a secondary fluid chamber;

FIG. 9 is a cross sectional view of the retention ring and sheath taken along section line 9—9 of FIG. 8;

FIG. 12–21 are related to another illustrative embodiment of the invention;

FIG. 12 is a perspective frontal view of the retention ring and retention ring insert;

FIG. 13 is a perspective view of the retention ring assembly positioned for mounting on a patient;

FIG. 14 is a perspective view of the fully assembled device mounted on a patient;

FIG. 15 is a perspective view of an alternative embodiment of the fully assembled device positioned for mounting on a patient;

FIG. 16 is a cross sectional view of the transitional section taken along section line 5—5 of FIG. 15;

FIG. 17 is a cross sectional view of the mounted urinary incontinence device taken along section line 6—6 of FIG. 14;

FIG. 18 is a cross sectional view of the transitional section taken along section line 7—7 of FIG. 17, with expandable flutes folded down by retention strap;

FIG. 19 is a cross sectional view of the transitional section as in FIG. 16 but with a larger inner diameter;

FIG. 20 is a cross sectional view of the assembled urinary incontinence device, similar to FIG. 17 but with a longer and larger diameter penis inserted;

FIG. 21 is a cross sectional view similar to FIG. 18 but with a larger diameter inner cylindrical section.

DETAILED DESCRIPTION OF ILLUSTRATIVE EMBODIMENTS

The present invention will be described herein with reference to illustrative embodiments of a male urinary incontinence device.

Figure 1:
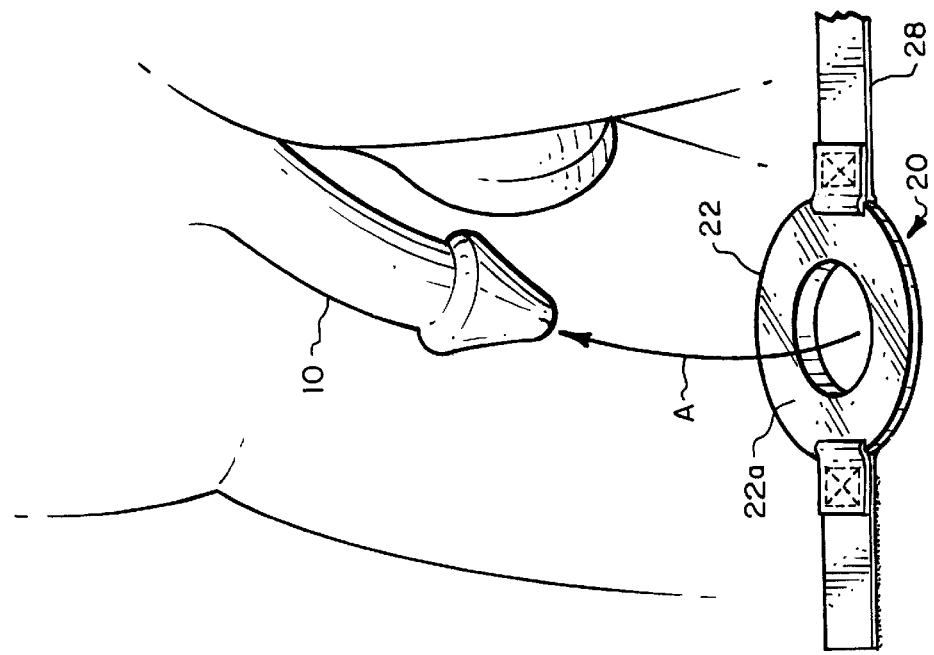
FIG. 1 is a perspective view of the retention ring positioned for mounting on a patient.
Figure 2:
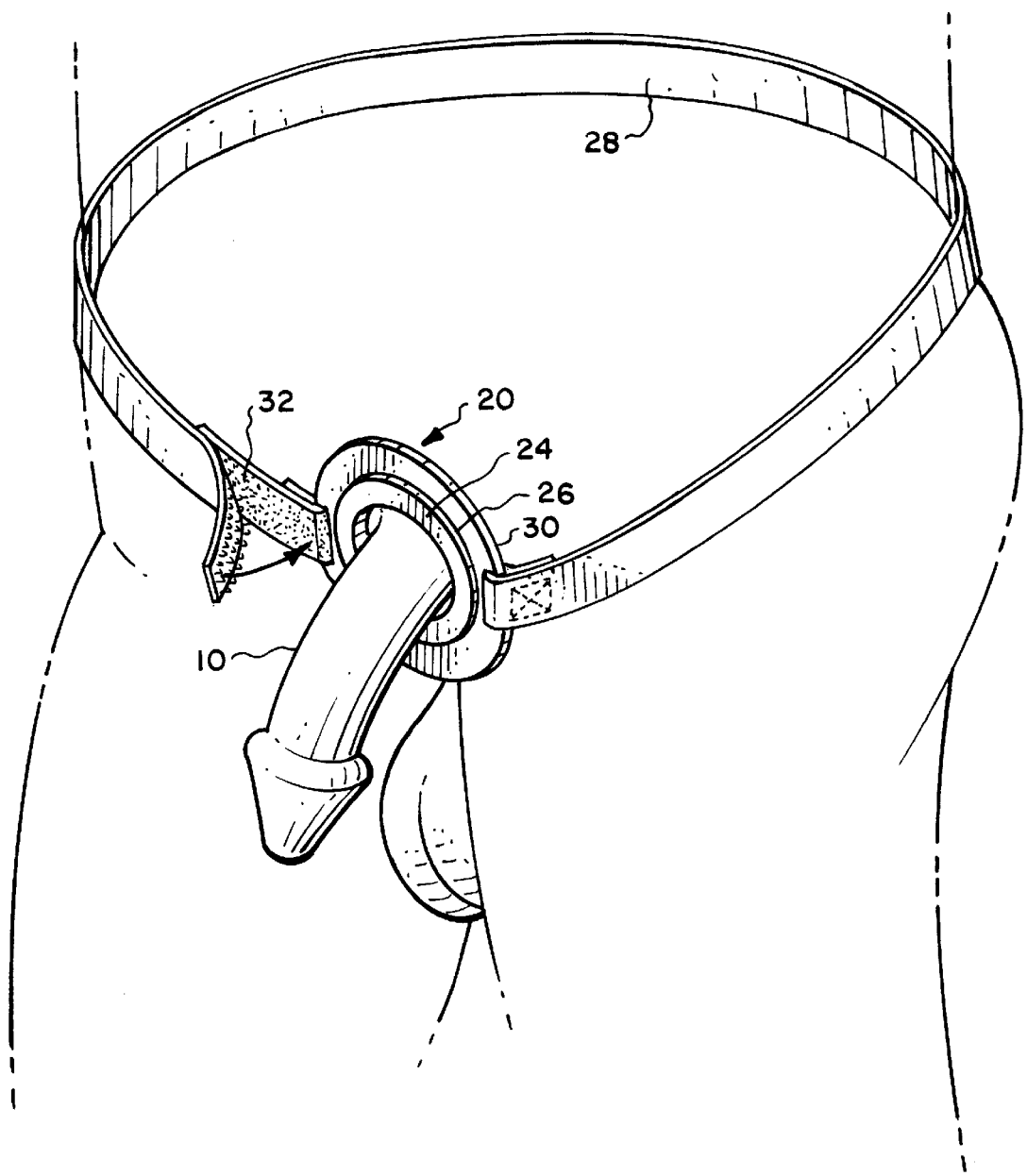
FIG. 2 is a perspective view of the retention ring mounted on a patient.

Referring to FIG. 1, the male patient is depicted having a penis 10. A retention assembly 20 is mounted to the patient as depicted by the arrow A and as further shown in the following Figures. The retention assembly 20 has a retention body 22, which is a generally flat or contoured member having a hole which accommodates the insertion of the penis therethrough. A flat side 22a of the retention body 22 is, in use, pressed against the body of the patient. A band 28 holds the retention body 22 to the patient in known fashion. In use, the penis is inserted in the hole of the retention body 22, and the band adjusted such that the flat side 22a of the retention body presses against the patient to the extent necessary to urge the penis 10 through the hole, as depicted in FIG. 2. In patients having a withdrawn penis due to obesity or other anatomic features, the retention body allows the penis to be urged through the hole to the extent necessary to attach the device, as will be discussed hereinbelow.

As further shown in FIG. 2, the band 28 passes through securing structures, such as slots 30, on the retention body 22. The band 28 is attached by a band attachment structure 32 which can be hook and loop fastener, adhesive, clasps, hooks, elastic, piton and hole arrangements, clips, clamps, strap locks, and the like. The band can be of any suitable material, either woven or otherwise, elastic or inelastic, based on the preferences of the user. The band can also be in the form of a garment, such as briefs, pants or the like.

Also depicted is an attachment flange 24, underlying which is a groove 26 which cooperates with retaining structure of a sheath wrap as discussed in greater detail hereinbelow.

The retention body 22 is depicted as being a hollow disk, but other shapes are of course possible. The outer peripheral shape of the retention body can be any shape which provides comfort, sufficient strength, and adequate attachment points for the band 28. The band 28, while illustrated as a waist band, can also attach to other anatomical features, for example the legs depending on the patient. The hole in the retention body should be wider than the penis, and provide adequate clearance in the case of an erection. The preferred material is high-impact molded plastic for strength, cost and ease of cleaning, but other materials such as metal, composites, and the like are also possible.

Figure 3:
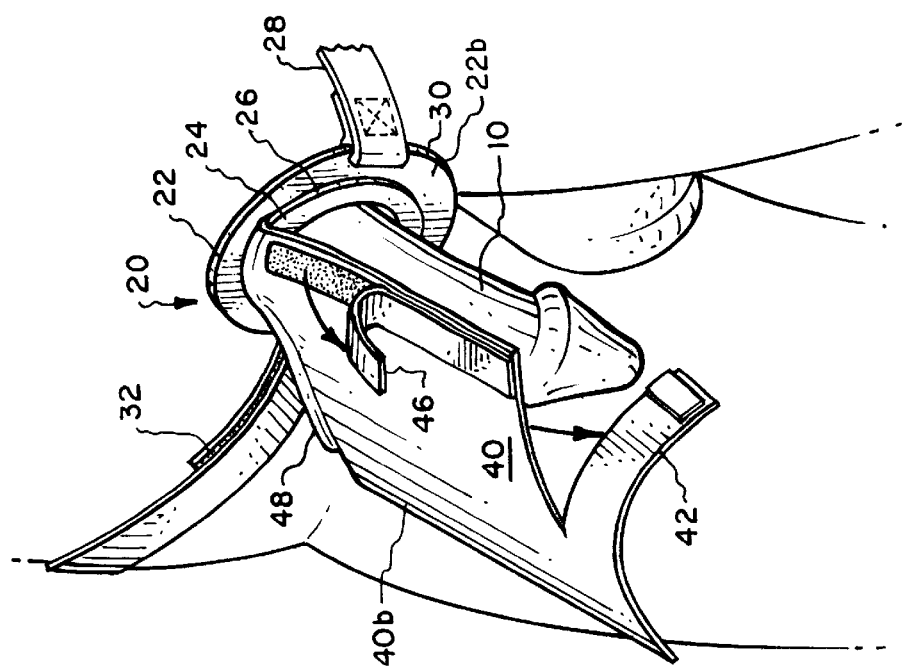
FIG. 3 is a perspective view of a wraparound sheath according to the invention being applied to the retention ring of FIGS. 1 and 2 and the patient.

Referring now to FIG. 3, the application of the sheath wrap 40 is depicted. The sheath wrap 40 is applied circumferentially about the phallus 10 to envelop the same. The sheath wrap is applied in contrast to a condom, which is unrolled up the shaft of the penis 10. The sheath wrap 40, being formed of a flexible sheet of material such as latex, urethane, or the like, can be easily trimmed to size, as depicted by extra material 42 being removed. Of course, indicia (not shown) can be positioned on the sheath wrap 40 to aid in trimming. Extending longitudinally down the sheath wrap is an attachment portion 44, which may be an adhesive strip provided with a removable backing 46. Of course other attachment means are usable, such as adhesives, hook and loop fasteners, and the like, or the sheath wrap can be treated over a portion of the surface to form a secure bond to a mating surface. Extending laterally across the proximal edge of the sheath wrap 40 is a sheath retention portion 48, which in the illustrative embodiment is in the form of a thickened bead portion stably receivable in the groove 26 of the retention body 22. In applying the sheath wrap 40 to the penis, the retention portion 48 may be pushed into the groove 26 of the retention body in a circular motion by the thumb, following the fingers which wrap the sheath around the penis. The penis is advantageously urged forth from the hole in the retention body, providing firm graspability of the penis shaft. After the sheath wrap 40 has surrounded the penis, the attachment portion 44 is activated and the sheath secured. In the illustrative embodiment, activation of the attachment portion 44 would comprise removing the adhesive backing 46 and pressing the opposite longitudinal region 40b to the exposed adhesive 44. The penis is thus enveloped in the sheath wrap. The retention portion 48 of the sheath wrap 40 can also be an adhesive ring, a Velcro® loop attachment, or other means known in the art.

It should be noted that although the overlap of the sheath portions extends between the distal and proximal ends in a longitudinal direction, the overlap can be of any convenient shape, and may even comprise horizontal tabs which are individually secured. For example, it may be convenient to have the longitudinal region 40b formed in a staggered or other irregular shape to aid in gripping during removal.

Figure 4:
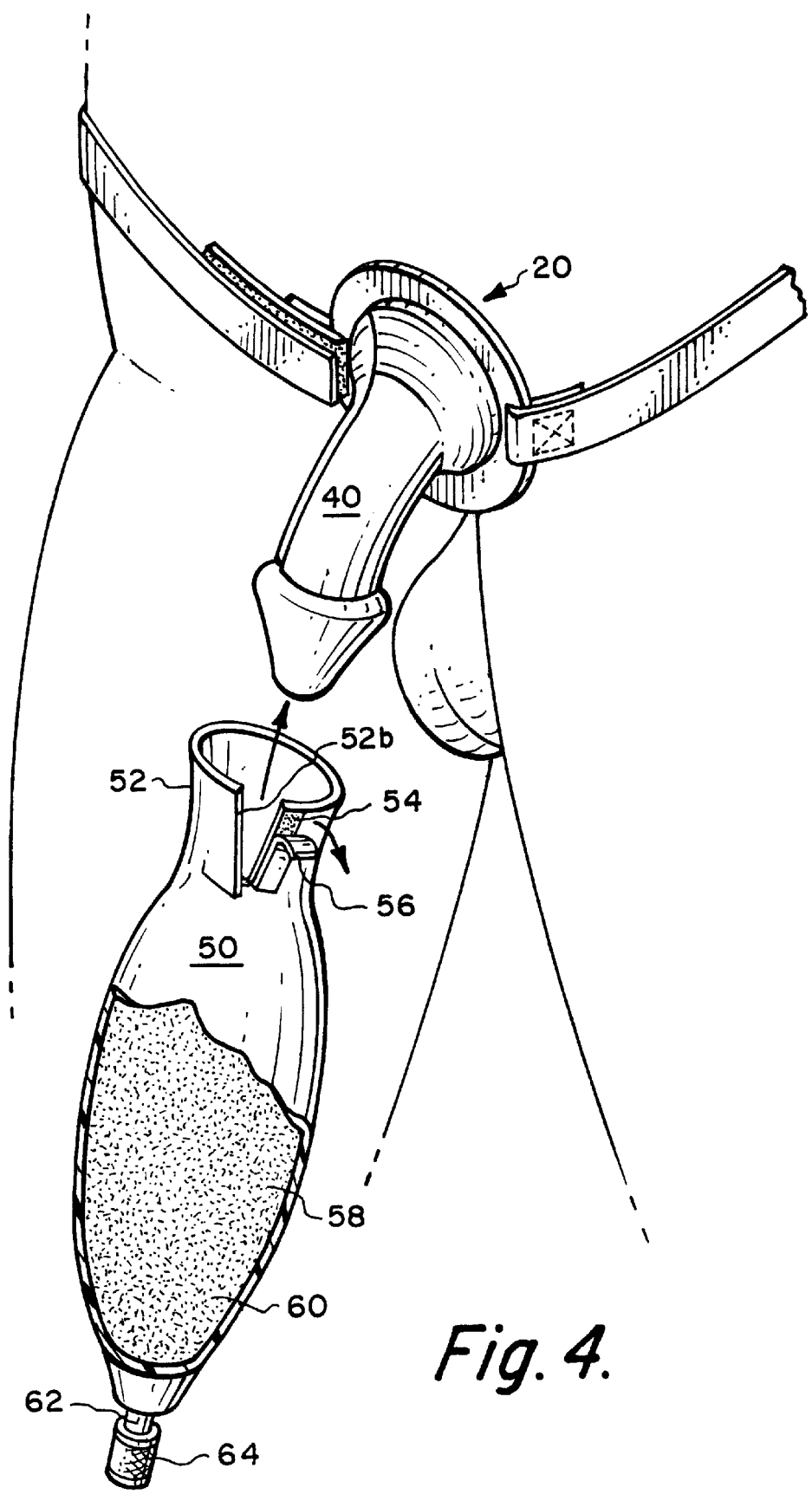
FIG. 4 is a perspective view of a primary fluid chamber positioned to attachment to the attached sheath of FIG. 3.

Referring now to FIG. 4, the penis 10 is depicted wrapped in the sheath 40, which is securely attached to the retention assembly 20. The sheath 40 now forms a stable, fluid tight surface for the mounting of the primary chamber 50, which receives urine expelled by the penis. As shown, the head of the penis is preferably left exposed, but the shaft is wrapped with the sheath, protecting the skin of the shaft from contact with urine. The primary chamber 50 is shown to comprise an attachment band 52, which can comprise a cylindrical inner diameter surface for engaging the sheath 40 deployed about the penis. The illustrative embodiment shows a split band 52, which can be opened to receive the penis 10 therein before securing the band around the sheath-enveloped penis shaft. Of course, other arrangements such as elastic is possible. The illustrative embodiment was designed for one-handed application. An attachment region 54 is provided, which may be an adhesive strip provided with a removable backing 56. Of course other attachment means are usable, such as adhesives, hook and loop fasteners, and the like, or the sheath wrap can be treated over a portion of the surface to form a secure bond to a mating surface. After the attachment band 52 has surrounded the ensheathed penis, the attachment portion 54 is activated and the sheath secured. In the illustrative embodiment, activation of the attachment portion 54 would comprise removing the adhesive backing 56 and pressing the opposite longitudinal region 52b to the exposed adhesive 54. The inside surface of the band 52 and the outside surface of the sheath 40 provide a good anti-slip, high-friction contact, which stably maintains the primary chamber 50 on the penis 10.

The primary chamber 50 forms an interior volume 58, which received urine from the penis. The interior volume may be initially empty, or may contain a gelling chemical known in the art which combines bioactive polymers and enzymes, which upon contact with the urine will gel it into a colloid or semisolid. The bottom portion of the primary chamber 50 can be provided with an emptying neck or tube 62, with a cap 64. Of course, the cap can be replaced with a cock or valve, or may be linked to a secondary chamber such as a bedside bag or reservoir, leg bag, or the like. When connected to a secondary chamber, a check valve and other connecting conduit hardware may be employed as well known in the art.

Figures 5, 6:
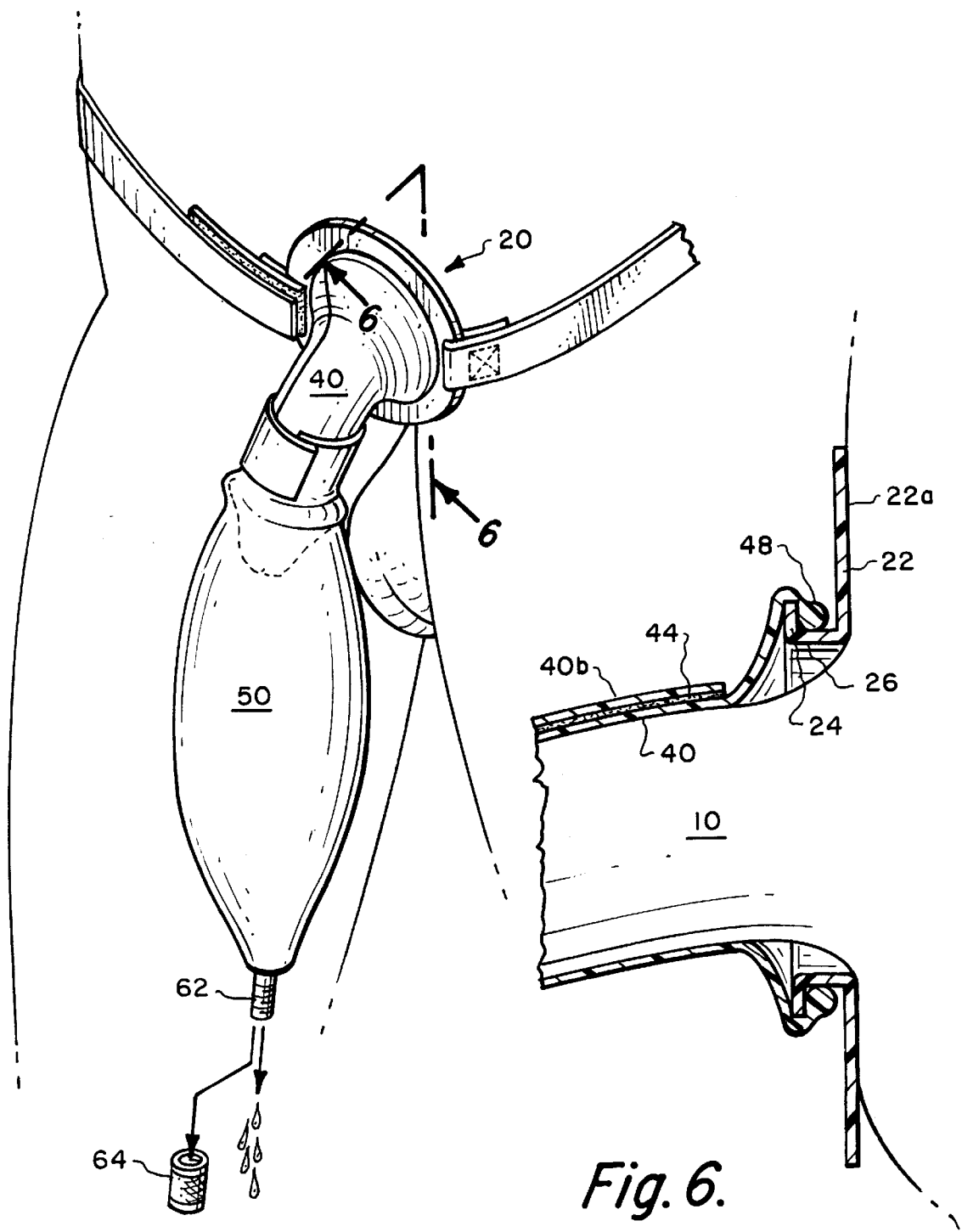
FIG. 5 is a perspective view of the primary fluid chamber of FIG. 4 attached to the sheath.
FIG. 6 is a cross sectional view of the retention ring and sheath taken along section line 6—6 of FIG. 5.

Referring to FIG. 5, the primary chamber 50 of FIG. 4 is shown fully mounted to the sheath wrap 40, surrounding the penis and attached to the retaining assembly 20. The urethra of the penis is therefore in fluid communication directly with the inner volume of the primary chamber. The cap 64, as shown, can be removed from the neck 62 to drain liquid from the interior of the primary chamber 50. The cap 64 is shown to be threadedly attached to the neck 62, but other attachment formats known in the art can be employed.

FIG. 6 is a cross section view taken along line 6—6 of FIG. 5. The attachment of the sheath wrap 40 to the retention assembly is shown in greater detail, revealing the illustrative embodiment. The retention body 22 is shown with a substantially flat side 22a positioned against the body, with the penis 10 extending through the central hole. The attachment flange 24 is shown to provide a groove 26, which receives therein the retention portion 48 of the sheath 40, which in the illustrative embodiment is a thickened bead portion. The sheath 40 is shown disposed about the penis 10, with the longitudinal edge 40b overlying a sheath wrap portion. The assembly is thus stably disposed about the penis.

Figure 7:
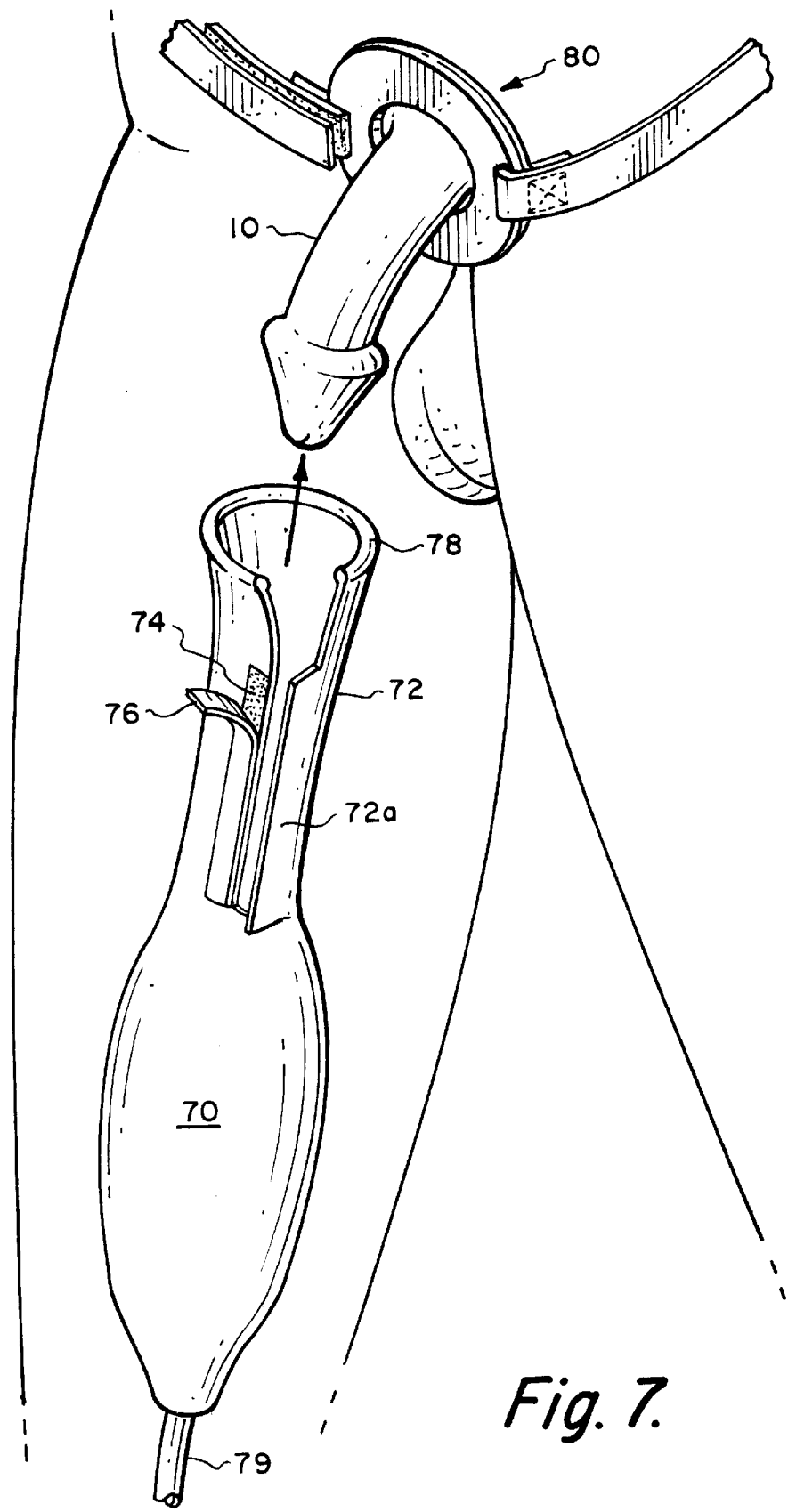
FIG. 7 is a perspective view of an integrated sheath and primary fluid chamber positioned for attachment to a patient.

FIG. 7 depicts an alternative embodiment 70 of the present invention where the primary chamber and the sheath wrap are integrated into a single piece. As above, the sheath portion is proximal and the primary chamber distal to the user. A sheath band 72 is provided to surround the penis 10 as above, where a longitudinal region 72a is positionable over a attachment region 74, which in the illustrative embodiment is an adhesive strip with a removable backing 76. A sheath retention portion 78 is disposed circumferentially about the sheath portion, and is receivable in a retention assembly 80, described below. A drain tube 79 can be formed in the bottom of the primary chamber. FIG. 8 depicts the alternative embodiment 70 of FIG. 7 mounted onto the penis, with tube 79 descending to a secondary chamber 90 in the form of a leg bag.

FIG. 9 is a cross section view taken along line 9—9 of FIG. 8. The attachment of the sheath wrap 70 to the retention assembly is shown in greater detail, revealing the alternative illustrative embodiment. The retention body 82 is shown with a substantially flat side 82a positioned against the body, with the penis 10 extending through the central hole. The attachment flange 84 is shown to provide a lip 86 that receives the retention portion 78 of the sheath 70, which in the illustrative embodiment is a thickened bead portion. The sheath 70 is shown disposed about the penis 10, with the longitudinal region 70a overlying a sheath wrap portion. The assembly is thus stably disposed about the penis. This embodiment of the retention body 82 dispenses with the flange of the earlier embodiment, and instead requires that the retention portion 78 of the sheath be applied about the outer circumference of the retention body 82 proper.

Of course, the retention assembly of FIG. 9 is not constrained for use with the integrated sheath and chamber 70 of FIGS. 7–8. The sheath/chamber combinations of this application may be used, when properly configured, in any combination with the retention assemblies herein disclosed.

Figure 10:
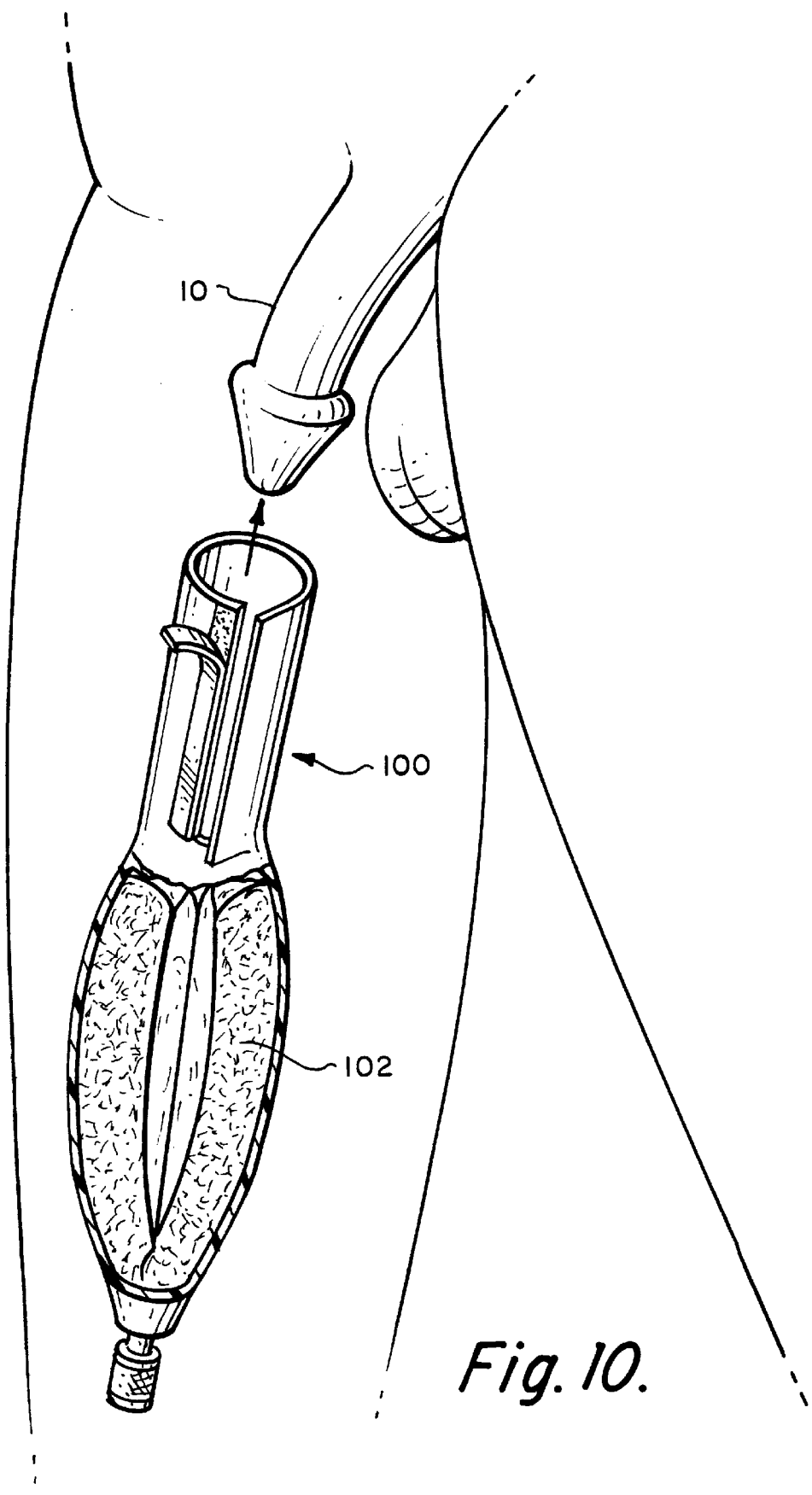
FIG. 10 is a perspective view of another embodiment of an integrated sheath and primary fluid chamber positioned for attachment to a patient.
Figure 11:
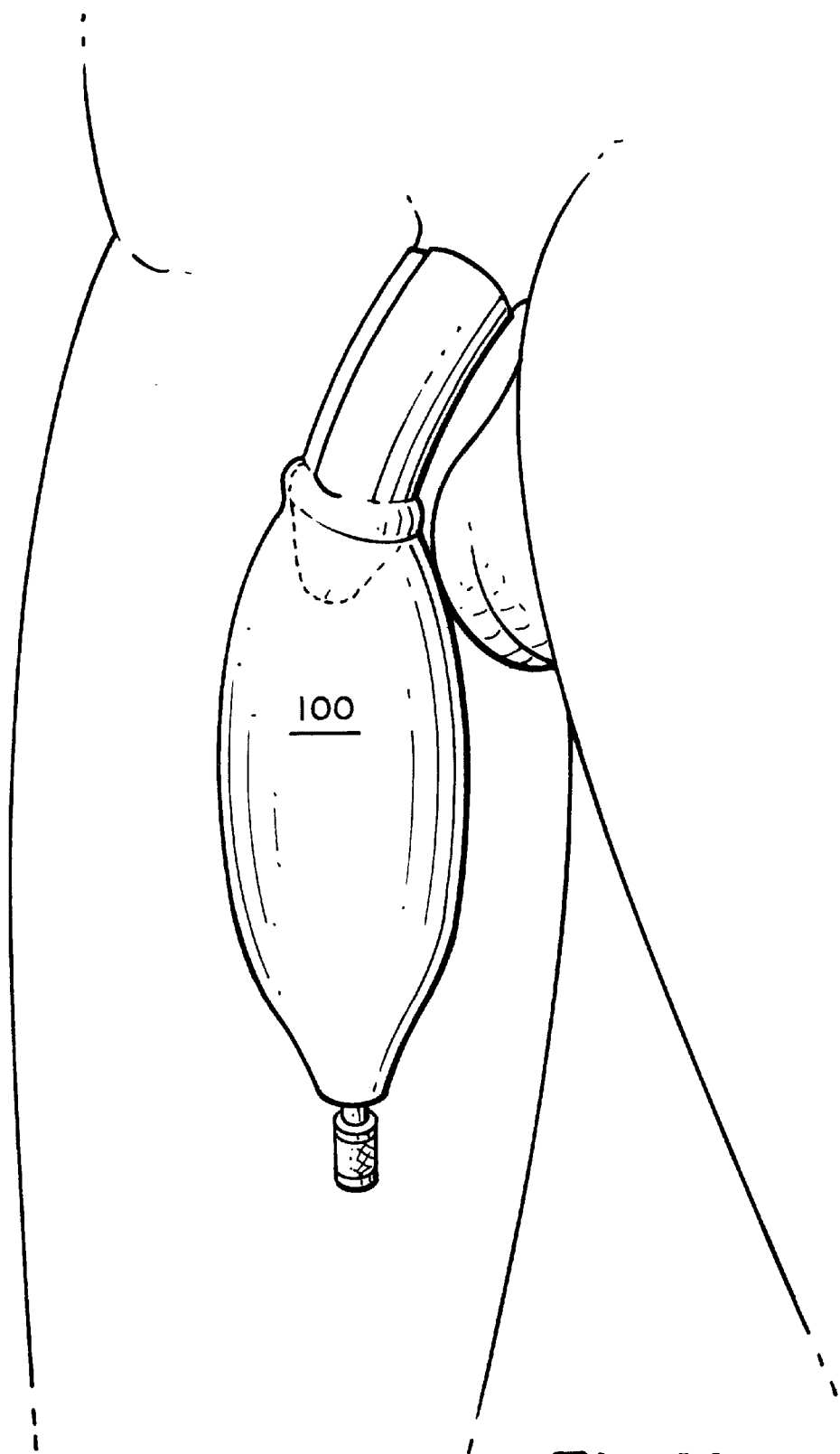
FIG 11 is a perspective view of the integrated sheath and primary fluid chamber of FIG. 10 mounted on a patient.

FIG. 10 depicts a third alternative embodiment of the present invention which does not require the use of a retention assembly. In this embodiment the combination sheath wrap and chamber 100 is configured substantially the same as the embodiment of FIG. 7, except that there is no retention portion on the sheath at the proximal end thereof. This embodiment is simply wrapped about the penis 10. Additionally, the interior of the chamber may be lined with an absorbent material 102. FIG. 11 depicts the third alternative embodiment being worn by a user.

In applying the invention as hereinabove described, each embodiment is attached to a penis by wrapping the penis in the sheath portion of the device in a circumferential fashion about the surface of the penile shaft. This is in contrast to a condom, which is applied by unrolling material longitudinally from the tip to the base of the penile shaft.

Another illustrative embodiment of the present invention will now be described.

Figure 12:
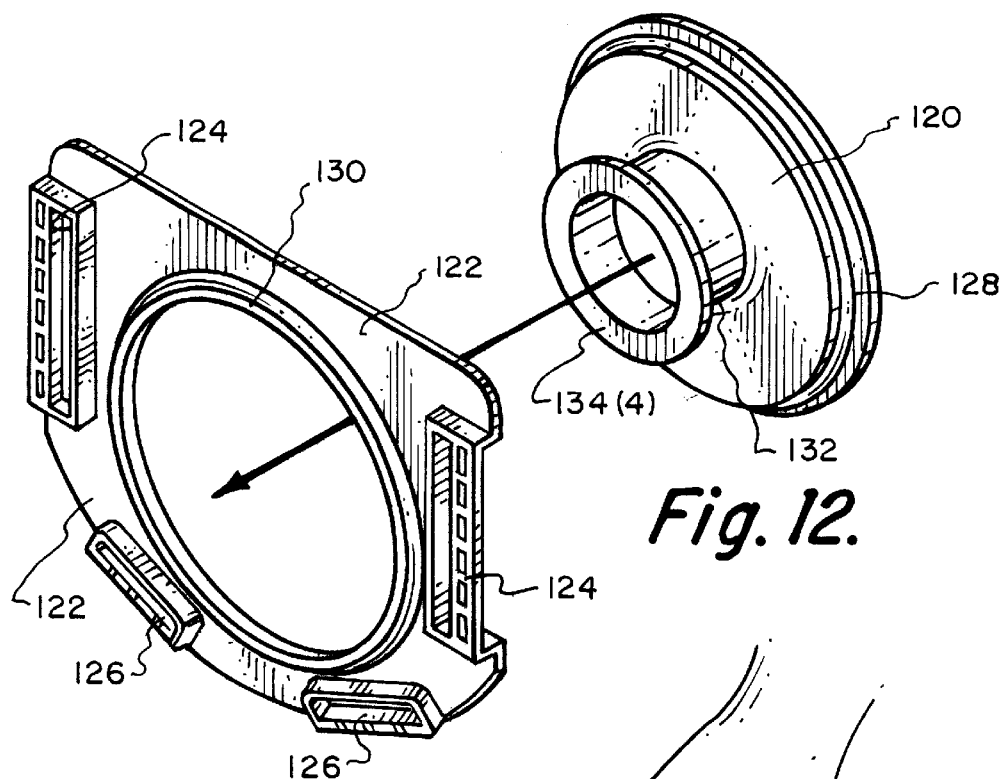

Referring to FIG. 12, the retention ring assembly is depicted having a retention ring (or plate) 122 and a retention ring insert 120. Retention ring 122 is a generally flat or contoured member having a standard-sized hole which accommodates the insertion of retention ring insert 120. Retention ring 122 and retention ring insert 120 can either be molded into a single entity or can be assembled so that retention ring insert 120 is fitted into the retention ring 122. In the case of the latter embodiment, retention ring insert 120 having an appropriate sized central aperture can be selected for a penis having a specific diameter and fitted into the master retention ring 122. In this way, the urinary incontinence device can be customized to provide a comfortable fit for individual penises. In either embodiment, master retention plate 122 has securing sites for retention straps or support straps. Waist band support straps are passed through openings 124 on each side of the plate and leg straps are passed through the lower portion 126 of the plate. If the retention ring 122 and retention ring insert 120 are separate components designed to be fitted together, the connection of the two parts can be accomplished by pressing, snapping, screwing, or by any other alternative means for engaging, for example, external periphery 128 of retention ring insert 120 with the internal periphery 130 of retention ring 122.

Figure 13:
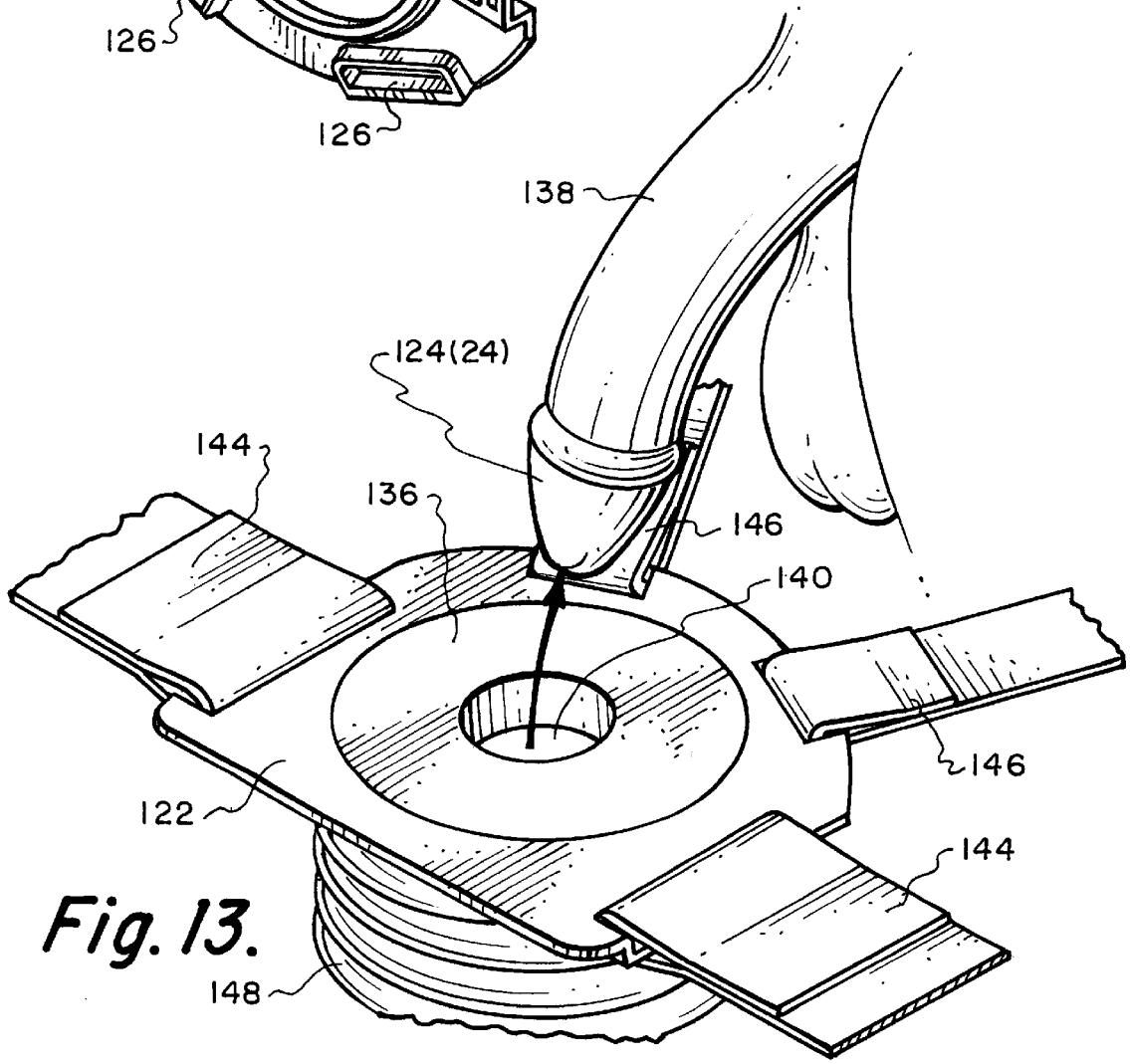

Referring now to FIG. 13, the rear side 136 of retention ring insert 120 is depicted assembled into the retention ring assembly 122, positioned for insertion of penis 138. Retention ring insert 120 has an opening 140 for insertion of penis head 142 and penis shaft 138. In addition, FIG. 13 depicts the waist band support strap 144 as passing through securing structure 124, on the retention ring 122, and the leg strap 146 as passing through securing structure 126. Various types of securing expedients can be used for attaching leg straps such as snaps, Velcro®, closures, clamps, or permanent affixation by gluing or welding, just to name a few. The band can be of any suitable material, either woven or otherwise, elastic or inelastic, based on the preferences of the user.

The retention ring 122 and retention ring insert 120 are depicted as being hollow disks, but other shapes are of course possible. The outer peripheral shape of the retention ring can be any shape which provides comfort, sufficient strength, and adequate attachment points for bands 146 and 144. The preferred material is high-impact molded plastic for strength, cost and ease of cleaning, but other materials such as metal, composites, and the like are also possible. The remaining part of the device 148 that encompasses the penis will be discussed in further detail herein below.

Figure 14:
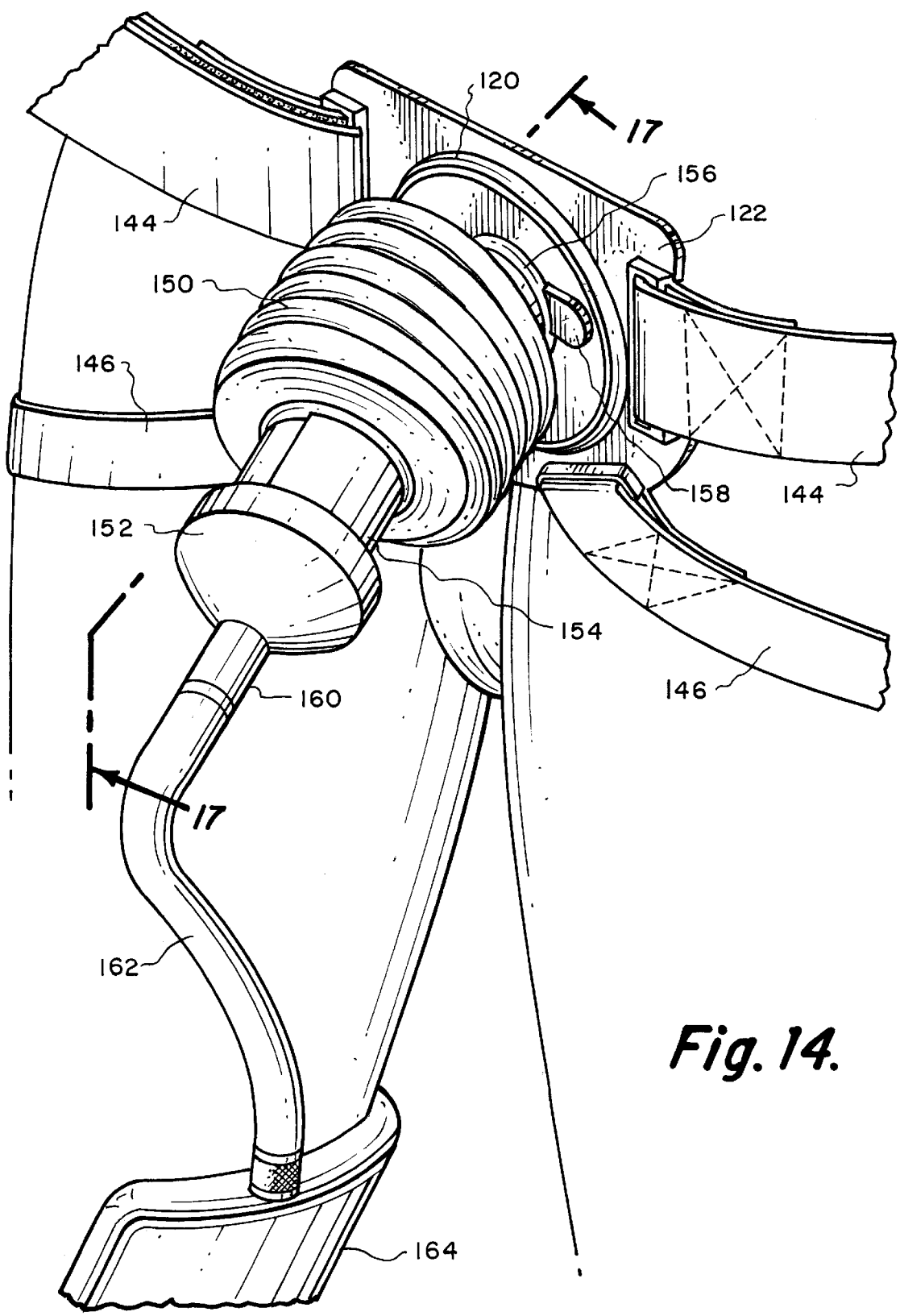

Referring now to FIG. 14, a fully pre-assembled device is mounted onto a penis. The penis is passed through the hollow region of retention ring assembly 120 and 122 and further pushed into the longitudinally compliant portion, shown in the illustrative embodiment as expansion bellows 150, until the head of the penis reaches a penile chamber 152 after passing through radially compliant portion 154 (a detailed discussion of which is presented below). Waist band 144 and leg strap 146 can then be wrapped around the patient in a known fashion. The remaining structure of the device enveloping the penis is secured onto the retention ring assembly 120 and 122 by a retention portion such as a thickened rubber ring 156 at the top of the expansion bellows 150 by being stretched over retention structure 132 (shown in FIG. 12). Although the retention structure is depicted as residing on the insert, it could also reside on the retention body as in the prior embodiment. The diameter of the ring 156 is smaller than the diameter of the retention structure 132 so that the ring 156 slips over a lip 134 (also depicted in FIG. 12) and is stretched over the retention structure 132. The ring 156 is held in place by the strength of the thickened band. Thus, the device can be placed over the penis without resistance of a flaccid penis and over any size retention ring assembly 120 and 122. It should be noted that the entire sheath body is preferably made of the same, flexible material, such as latex, silicone, urethane or a similar medical grade material, which will exhibit some degree of elasticity, and therefore longitudinal and radial compliance by virtue of the material. Expansion bellows 150 and 154 are specifically designed to provide for far more compliance than could radially compliant portion be realized by virtue of the material alone.

Tabs such as 158 can be added to assist in stretching of the rubber ring over retention structure 132. Additional tabs or other alternative means can be utilized in order to ease the ring 156 onto the retention structure 132. These tabs and other means can also ease the removal of the device from the retention structure 132.

The expansion bellows 150 can be fully compressed as well as fully extended, in an accordion-like manner, to accommodate any change in penile length. Changes in penile length can be caused by swelling, penile erection, and the like. Penile chamber 152 conforms to the shape of the head of the penis. It can further have a somewhat conical shape extending out distally so that no urine will flow retrograde up the penis but rather is encouraged to flow out naturally. A nozzle 160 at the end of the penile chamber 152 allows for attachment of urine collection bags, chambers or the like. The nozzle 160 can further have a valve of different types. For example, a cap can be attached to prevent leakage, an anti-reflux valve can be utilized to prevent back flow of urine when, for instance, the patient were lying down, or a securing device to further allow attachment of extension tubing such as the one illustrated as 162. Any number of collection tubes, bags or chambers 164 can be used for the collection of urine.

Figure 15:
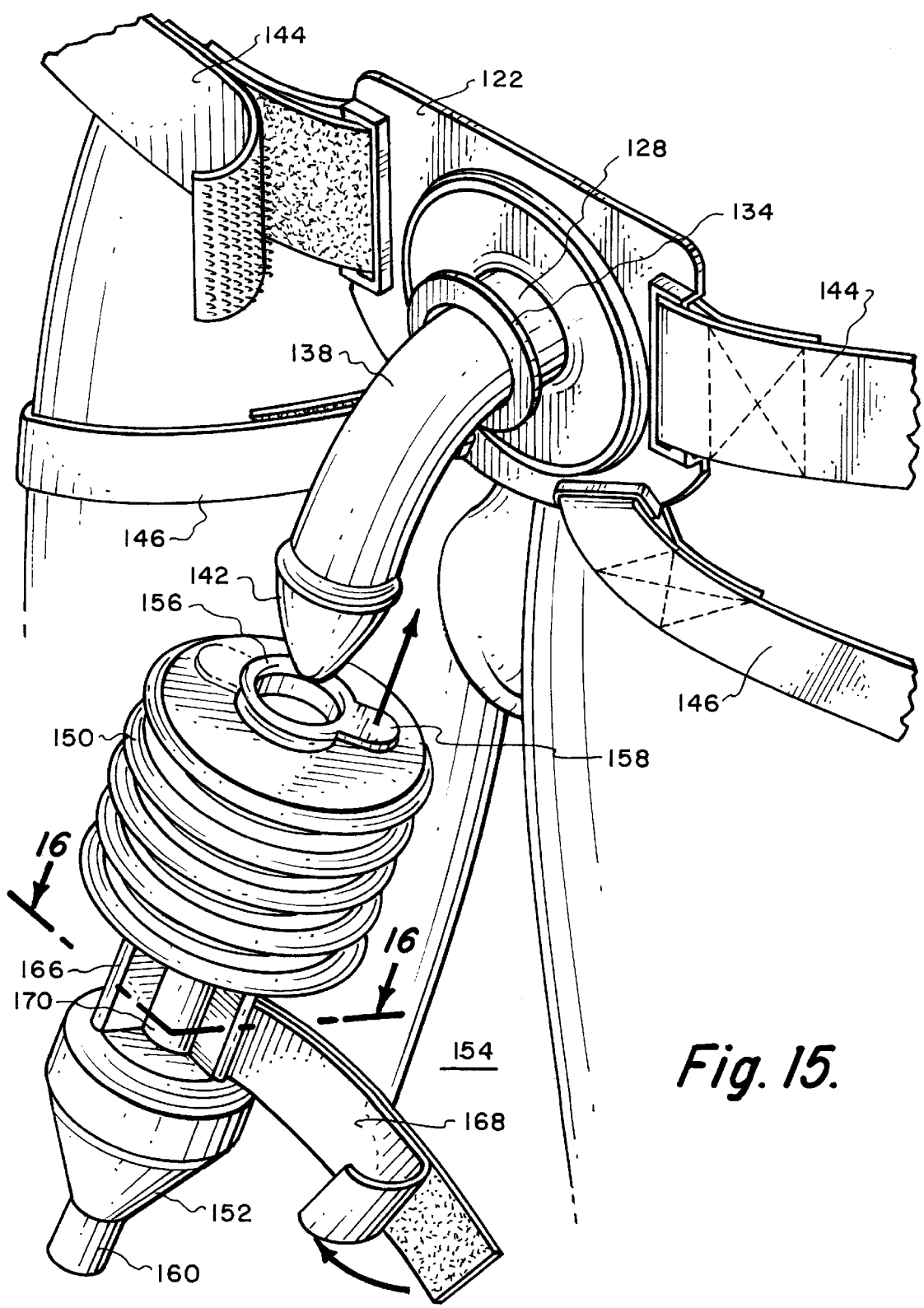

Referring now to FIG. 15, an alternative embodiment of the urinary incontinence device is depicted, in which each part of the device is assembled separately onto the penis, rather than being mounted onto the penis as a fully pre-assembled device. First, the retention ring 122 with attached retention ring insert is mounted onto the base of the penis 138. Waist strap band 144 and leg strap 146 are wrapped around the patient to secure the retention ring assembly. The expansion bellows 150 is slid onto the penis and secured onto the retention ring assembly by stretching the thickened rubber ring 156 that can be at the top of expansion bellows 150 over lip 134 of retention structure 128. Tabs 158 can also be used to assist the stretching of the rubber ring 156 over the lip 134 and securing the rubber ring 156 onto the retention structure 128. The lip 134 can have various shapes for various types of devices to be attached.

A radially compliant portion 154 further accommodates differences in penile size. The radially compliant portion 154 can have expandable flutes 166, a contractible inner cylindrical section 170, and a retention strap 168, all of which will be explained in detail herein below in FIGS. 16 and 18.

FIG. 16 is a cross sectional view of the transitional section taken along line 5—5 in FIG. 15. When the penis is inserted through the expansion bellows 150, the penis experiences no resistance since the expansion bellows 150 have the largest diameter in the device. In order to provide a gentle and expandable grasp on the penis, the radially compliant portion 154 is placed just behind the penile gland or the head 142 of the penis, as seen in a cross sectional view of the fully mounted device in FIG. 17. When the head of the penis 142 comes in contact with the small inner cylindrical section 170, the expandable flutes 166 will separate and open up to give a larger diameter opening if necessary.

FIG. 17 is a cross sectional view of the urinary incontinence device depicted in FIG. 14. FIG. 18 is a cross sectional view of the transitional section taken along the section line 7—7 of FIG. 17. Depicted is with the expandable flutes 166 strapped and folded down along inner cylindrical section 170, and held in place with means for retention, such as strap 168.

The retention strap 168 can also be attached to the expandable flutes 166 or to the inner cylindrical section 170, thereby providing a starting point for wrapping the expandable flutes 166 around the penis. The retention strap 168 can then be used to collapse the excess flute material 166 flat onto itself and proceed to wrap around the penile shaft, so as to provide a tight seal around the penis. The retention strap 168 can be provided attached to the device or be separately available for attachment after the sheath has been placed over the penis. The retention strap 168 can be secured by various methods, such as Velcro®, adhesive strips, adhesive paste, or any other additional methods.

Figure 19:
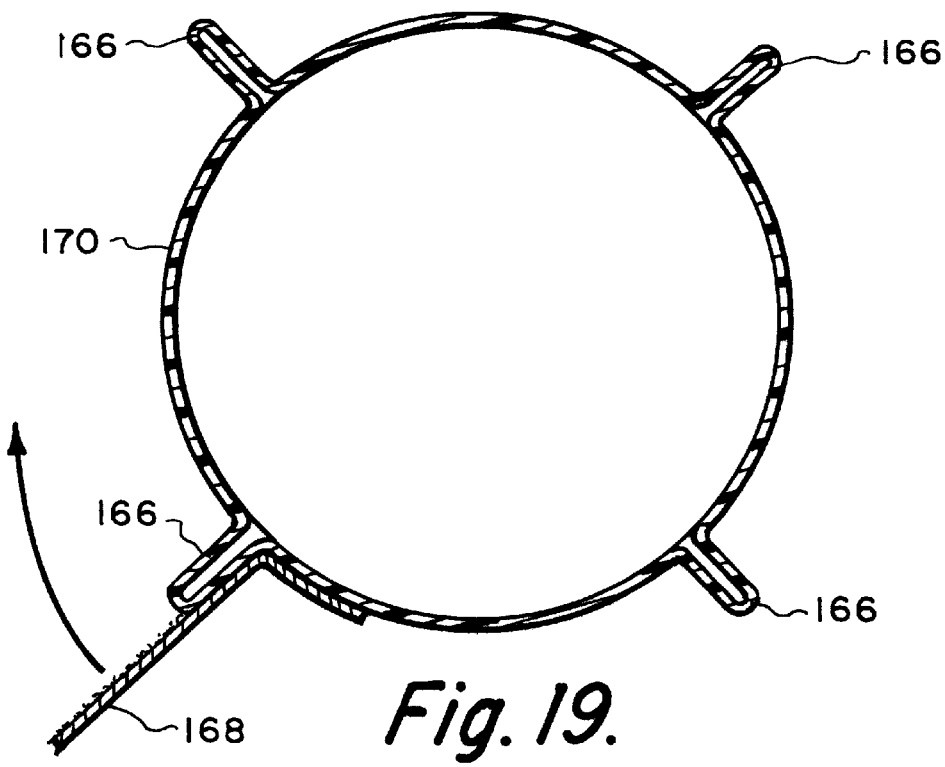
Figure 21:
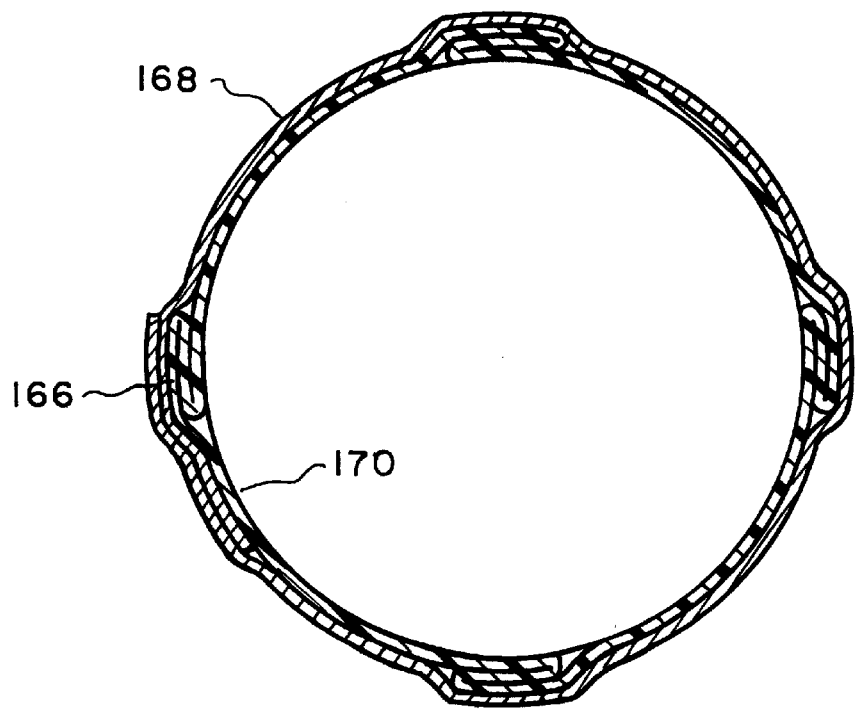
Figure 20:
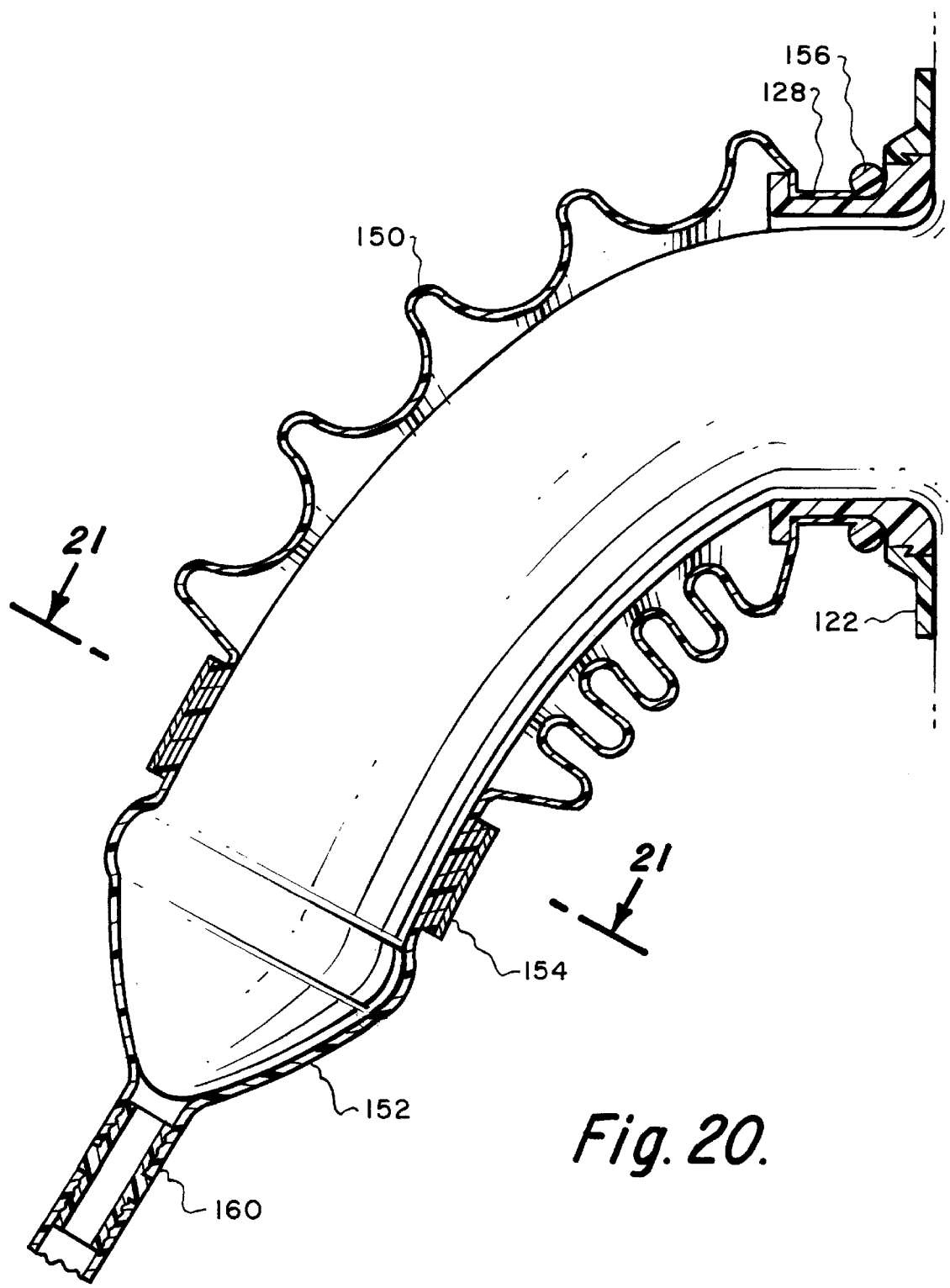

FIG. 19 illustrates the change in dimension of the transitional section 154 as a result of an increase in the diameter of inner cylindrical section 170. The expandable flutes 166 become smaller as the diameter of the inner cylindrical section 170 increases. More surface area covering the penis is now shown. The retention strap 168 can then be wrapped around the penile shaft just behind the head of the penis, which will collapse the remaining material in the flutes and will fold down onto the circumference of the penile shaft, as depicted in FIG. 21. In comparison, FIG. 18 illustrates the more extensive wrapping of the retention strap 168 around the circumference due to a smaller inner cylindrical section 170 diameter. The retention strap 168 can be secured by various methods, such as Velcro®, adhesive strips, adhesive paste, or any other additional methods. The material used for the transitional section 154 will allow for a stretching effect, and not cause any constriction around the shaft 138 of the penis. This feature allows for another mechanism, in addition to the expansion of the expansion bellows 150 as depicted in FIG. 20, by which enlargement of the penis (length, by the expansion bellows 150, and diameter by the radially compliant portion 154) can be accommodated in the case of swelling, penile erection, or other conditions which may cause enlargement. In FIG. 20, expansion bellows 150 are depicted as being stretched in comparison to those depicted in FIG. 17. This stretching of the expansion bellows 150 illustrates the mechanism by which the urinary incontinence device accommodates an enlargement of the length of the penis.

FIG. 21 illustrates the second mechanism by which the urinary device is capable of size changes of the penis. Depicted is the radially compliant portion 154 with a large inner diameter of the inner cylindrical section 170 in comparison to that of FIG. 18. Less expandable flutes 166 are available due to stretching by an enlarged penis, yet are held in place with the retention wrap 168.

In another embodiment, the retention ring 122 can be placed inside the liner of a pant or undergarment, eliminating the need for retention waist band 144 and/or leg strap 146. Retention ring insert 120 can be provided pre-assembled with the retention ring 122 or it can be manually placed into retention ring 122. Retention structure 128 of retention ring insert 120 can be exposed from the clothing so that the thickened rubber ring 156 can be stretched over retention structure 128 in order to secure the remainder of the urinary device onto retention ring assembly 122 and 120. In this way, proper alignment of the device over the penis can be maintained without the need for additional securing mechanisms.

Other devices may also be used in combination with the invention herein described. For example, moisture monitors may be used with the present invention to train against bedwetting and other types of incontinence. In use, a sensor port could be provided in the sheath or primary chamber, or in the drain tube at the distal end of the primary chamber.

Although the invention has been shown and described with respect to exemplary embodiments thereof, various other changes, additions and omissions in the form and detail thereof may be made therein without departing from the spirit and scope of the invention. In addition to the exemplary changes suggested hereinabove, it should also be noted that the various features for managing the urine directed into the interior of the primary chambers hereinabove discussed, viz., absorbent, gelling chemical, tubes, valves, caps, and the like, may be used in any combination with any of the devices herein described, and should not be construed as limited to the specific embodiments which provide context for their exhibition herein.

What is claimed is:

1. An apparatus for forming a fluid tight wrap around a penis of a user comprising:

a substantially fluid impermeable sheath for forming a fluid tight wrap around a penis of a user having a proximal end and a distal end, an inner surface and an outer surface, wherein, in use, at least a portion of the inner surface contacts the skin of the penis;

said sheaf further having a first longitudinally compliant portion and a second radially compliant portion positioned between said proximal and distal ends;

wherein said longitudinally compliant portion automatically and instantaneously collapses and extends as needed without resistance to accommodate for changes in penile length and said radially compliant portion comprises a contractible, inner section and a plurality of expandable flutes, which automatically and instantaneously compress and expand as needed to accommodate for changes in penile diameter while maintaining said fluid tight wrap at said distal end.

2. The sheath of claim 1, wherein said radially compliant portion further comprises a retention means for retaining said radially compliant portion about the circumference of the penis of a user in a fluid tight manner.

3. A method for applying a sheath to a penis of a user comprising the steps of:

first providing a retention assembly having a hole herein to a user, the hole for receiving a penis shaft of a user, said retention assembly further comprising a retention structure for securing the proximal end of the inner surface of the sheath to the distal side of the retention assembly;

next providing a sheath having a proximal end and a distal end, an inner surface and an outer surface, the sheath having a first longitudinally compliant portion and a second radially compliant portion positioned between said proximal and distal ends such that said longitudinally compliant portion automatically and instantaneously collapses and extends as needed without resistance to accommodate for changes in penile length and said radially compliant portion automatically and instantaneously compresses and expands as needed to accommodate for changes in penile diameter while maintaining said fluid tight wrap at said distal end; and, then releasably securing the proximal end of the inner surface of the sheath to the distal side of the retention structure, such that said sheath may be rapidly removed from said retention structure and exchanged while both said retention structure and said retention assembly remain secured to the body of the user.

4. The method of claim 3, wherein said radially compliant portion of said sheath further comprises a retention means for retaining said radially compliant portion about the circumference of the penis of a user in a fluid tight manner, and wherein said method further comprises the step of securing said retention means.

5. The method of claim 3 further comprising the step of applying the sheath to the penis of a user prior to the step of securing.

6. The method of claim 3, wherein said step of providing a retention assembly further comprises selectably providing an insert, and wherein said securing step further comprising securing the proximal side of the sheath to the insert.

7. A urinary incontinence device comprising:

a substantially fluid impermeable sheath for forming a fluid tight wrap around a penis of a user having a proximal end and a distal end, an inner surface and an outer surface, wherein, in use, at least a portion of the inner surface contacts the skin of the penis;

said sheath further having a first longitudinally compliant portion and a second radially compliant portion positioned between said proximal and distal ends, wherein said radially compliant portion automatically and instantaneously compresses and expands as needed to accommodate for changes in penile diameter while maintaining said fluid tight wrap at said distal end, said radially compliant portion further comprising a contractible, inner section, a plurality of expandable flutes and a retention means for retaining said radially compliant portion about the circumference of the penis of a user in a fluid tight manner.

8. A urinary incontinence device comprising comprising:

a substantially fluid impermeable sheath for forming a fluid tight wrap around a penis of a user having a proximal end and a distal end, an inner surface and an outer surface, wherein, in use, at least a portion of the inner surface contacts the skin of the penis;

said sheath further having a first longitudinally compliant portion and a second radially compliant portion positioned between said proximal and distal ends, wherein said radially compliant portion further comprises a contractible inner section and a plurality of expandable flutes which automatically and instantaneously compress and expand as needed to accommodate for changes in penile diameter while maintaining said fluid tight wrap at said distal end.

9. The urinary incontinence device of claim 8, further comprising a chamber positioned between said distal end and said radially compliant portion.

10. The urinary incontinence device of claim 8, wherein said longitudinally compliant portion comprises a self-adjusting expansion bellows.

11. The urinary incontinence device of claim 8, wherein said radially compliant portion comprises a contractible inner section and a plurality of expandable flutes which collapse and expand to accommodate for changes in penile diameter.

12. The urinary incontinence device of claim 8 further comprising a retention assembly for surrounding the shaft of a penis of a user at a proximal end thereof, the retention assembly being secured to the body of a user and having a hole for receiving the penile shaft of a user to distally extend the same, the retention assembly further comprising a retention structure for securing the proximal end of the inner surface of the sheath to the distal side of the retention assembly.

13. The urinary incontinence device of claim 12, wherein the sheath member further comprises a retention portion at the proximal end thereof for cooperatively engaging the retention structure of the retention body.

14. The urinary incontinence device of claim 13, wherein the retention portion of the sheath comprises a thickened portion.

15. The urinary incontinence device of claim 14, wherein the retention portion comprises a flange having a groove.

16. The urinary incontinence device of claim 14, wherein the retention portion comprises a lip.

17. The urinary incontinence device of claim 14, wherein said retention assembly comprises a retention ring having an opening, and an insert selectably received in said opening, said insert having a hole for receiving the shaft of the penis of a user.

18. The urinary incontinence device of claim 12, wherein the retention structure is on said insert.

* * * * *